US007862823B1

(12) United States Patent
Leroy

(10) Patent No.: US 7,862,823 B1
(45) Date of Patent: Jan. 4, 2011

(54) MULTIVALENT VACCINE COMPOSITION WITH MIXED CARRIER

(75) Inventor: Odile Leroy, Garches (FR)

(73) Assignee: Sanofi Pasteur S.A., Lyons (FR)

( * ) Notice: Subject to any disclaimer, the term of this patent is extended or adjusted under 35 U.S.C. 154(b) by 0 days.

(21) Appl. No.: 09/423,698

(22) PCT Filed: May 14, 1998

(86) PCT No.: PCT/FR98/00966

§ 371 (c)(1),
(2), (4) Date: Feb. 10, 2000

(87) PCT Pub. No.: WO98/51339

PCT Pub. Date: Nov. 19, 1998

(30) Foreign Application Priority Data

May 14, 1997 (FR) .................................. 97 06210

(51) Int. Cl.
*A61K 39/385* (2006.01)
(52) U.S. Cl. ................................ 424/197.11; 424/244.1
(58) Field of Classification Search .............. 424/197.1, 424/184.1, 193.1
See application file for complete search history.

(56) References Cited

U.S. PATENT DOCUMENTS 4,372,883 A * 2/1983 Matuhashi et al.
5,623,057 A * 4/1997 Marburg et al.

FOREIGN PATENT DOCUMENTS

| EP | 0 497 525 | 8/1992 |
| WO | 88/00056 A1 | 1/1988 |
| WO | WO 88 00056 | 1/1988 |
| WO | 03/051392 A2 | 6/2003 |

OTHER PUBLICATIONS

Ahman et al (Pediatr. Infect. Dis. J. 15:134-9, 1996).*
Anderson et al (J. Pediatr. 128:649-53, 1996).*
Lee et al (Vaccine, 13(16):1533-1538, 1995).*
C. Chu et al.: "Further Studies on the Immunogenicity of *Haemophilus influenzae* Type B and Pneumococcal Type 6A Polysaccharide-Protein Conjugates", *Infection and Immunity*, vol. 41, No. 1, Apr. 1983, pp. 245-256.

D.P. Greenberg et al.: "Factors Influencing the Immunogenicity of a Pneumococcal Conjugate Vaccine in Infants", *Pediatric Research*, vol. 41, May 2-6, 1997, p. 121A.
G.R. Siber: "Pneumococcal Disease: Prospects for a New Generation of Vaccines", *Science*, vol. 265, Sep. 2, 1994, pp. 1385-1387.
C.C.A.M. Peeters et al.: "Effect of Carrier Priming on Immunogenicity of Saccharide-Protein Conjugate Vaccines", *Infection and Immunity*, vol. 50, No. 10, Oct. 1991, pp. 3504-3510.
R. Dagan et al.: "Reduced Response to Multiple Vaccines Sharing Common Protein Epitopes That Are Administered Simultaneously to Infants", *Infection and Immunity*, vol. 66, No. 5, May 1998, pp. 2093-2098.
Wuorimaa, T. et al., "Tolerability and Immunogenicity of an 11-Valent Pneumococcal Conjugate Vaccine in Adults." *Vaccine*. 19, pp. 1863-1869 (2001).
Wuorimaa, T. et al. "Tolerability and Immunogenicity of an Eleven-Valent Pneumococcal Conjugate Vaccine in Healty Toddlers." *Pediatr. Infect. Dis. J.* 20(3), pp. 272-277 (Mar. 2001).
Åhman, H. et al. "Dose Dependency of Antibody Response in Infants and Children to Pneumococcal polysaccharides Conjugated to Tetanus Toxoid." *Vaccine*. 17, pp. 2726-2762;(1999).
Fattom, A. et at "Epitopic Overload at the Site of Injection May Result in Suppression of the Immune Response to Combined Capsular Polysaccharide Conjugate Vaccines." *Vaccine*. 17, pp. 126-133 (1999).
Dagan, R. et al. "Reduced Response to Multiple Vaccines Sharing Common Protein Epitopes That Are Admilstered Simultaneously to Infants." *Infection and Immunity*. 66(5), pp. 2093-2098 (May 1998).
Eick et al., "Safety and Immunogenicity of Two Octavalent Pneumococcal Conjugate Vaccines in American Indian Infants", Vaccine 22, 2004, 1260-1264, Elsevier.
Nurkka et al., "Serum and Salivary Anti-Capsular Antibodies in Infants and Children Vaccinated With Octavalent Pheumococcal Conjugate Vaccines, PncD and PncT", Vaccine 20, 2002, 194-201, Elsevier.
Marie-Paule Schitze et al.: "Carrier-Induced Epitopic Supperssion, A Major Issue for Future Synthetic Vaccines," The Journal of Immunology, vol. 135, No. 4, Oct. 1985, pp. 2319-2322.
Marie-Paule Schutze et al.: "Carrier-Induced Epitopic Suppression is Initiated Through Clonal Dominance," The Journal of Immunology, vol. 142, No. 8, Apr. 15, 1989, pp. 2635-2640.

(Continued)

*Primary Examiner*—Patricia A Duffy
(74) *Attorney, Agent, or Firm*—McDonnell Boehnen Hulbert & Berghoff LLP

(57) ABSTRACT

The invention concerns a pharmaceutical composition for treating or preventing a certain number of infections caused by pathogenic agents such as bacteria, comprising as immunogen, one or several polyosides derived from one or several pathogenic agents. The polyosides are in the form of conjugates, coupled with a carrier protein. The composition contains at least two types of conjugates, each being at least characterised by a different protein carrier.

9 Claims, No Drawings

OTHER PUBLICATIONS

Carla C. A. M. Peeters, et al.: "Effect of Carrier Priming on Immunogenicity of Saccharide-Protein Conjugate Vaccines," Infection and Immunity, Oct. 1991, vol. 59, No. 10, pp. 3504-3510.

Ortqvist et al., "Pneumococcal Capsular Polysaccharide Vaccine (PCPV) for Prevention of Pneumonia in Middle-Aged and Elderly Persons: A Prospective, Randomized, Placebo-Controlled Multicenter-Trial", Abstracts of the 36th ICAAC, 1 page, Tuesday Session 61, Nabi-Rockville, USA.

Lindberg AA, 1999, Vaccine, 17:S28-S36.

Ahman et al., 1996, 36th Intersc Conf Animicrob Agents and Chemotherapy, New Orleans, Abstr. G109, p. 162.

Assess the Immunogenicity of GSK Biological's 10-valent Pneumococcal conjugate, retrieved from the Internet on Sep. 20, 2007, http://www.clinicaltrials.gov/ct/show/NCT00307541.

Wuorimaa et al., Scand. J. Immunol. 56, 111-129, 2002.

Steinhoff, M.C. et al. (1994) A randomized comparison of three bivalent *Streptococcus pneumoniae* glycoprotein conjugate vaccines in young children: effect of polysaccharide size and linkage characteristics. Pediatr. Infect. Dis. J. vol. 13 (5), pp. 368-372.

Chiu, S.S. et al. (1995) Safety and immunogenicity of a pentavalent pneumococcal conjugate vaccine (PPCV) in healthy toddlers. Presented at the 35th Intersc. Conf. Antimicrob. Agents and Chemotherapy, San Francisco Abstr G71, p. 171.

Daum, R.S. et al. (1995) Immunogenicity of *S Pneumoniae* oligo- and polysaccharide- CRM197 conjugate vaccines in healthy US infants. Presented at the 35th Intersc Conf. Antimicrob. Agents and Chemotherapy, San Francisco Abstr G 65, p. 170.

O'Brien, K.L. et al. (1996) Immunologic priming of young children by pneumococcal glycoprotein conjugate but not polysaccharide, vaccines Peditar. Infect. Dis. J. vol. 15 (5) pp. 425-430.

Rennels, M.B. et al. (1996) Abstract from Immunogenicity and Safety of 7-Valent Pneumococcal-CRM-197 Conjugate Vaccine. Pediatric Research, vol. 39 (4) part 2, p. 183A. Asbtr 1082.

Shelly, M.A. et al. (1997) Comparison of pneumococcal polysaccharide and CRM197 conjugated pneumococcal oligosaccharide vaccines in young and elderly adults Infection & Immunity vol. 65(1) pp. 242-247.

Kennedy, D. et al. (1994) Immunologic response of 12-18 months old children to licensed pneumococcal polysaccharide vaccine (PS) primed with *Streptococcus pneumoinae* 19F conjugate vaccine (CV). Presented at the 34th Intersc Conf. Antimicrob. Agents and Chemotherapy Orlando Abstract G88, p. 236.

Nieminen, T. et al. (1994) Mucosal and serum immune response to tetravalent pneumococcal (SPn) conjugate vaccines (SpnD and SpnT) in adults. Presented at the 34th Intersc. Conf. Antimicrob. Agents and Chemotherapy Abstract G89, p. 236.

Portier, H. et al. (1994) Serum antibody response to a tetravalent pneumococcal tetanus toxoid conjugate vaccine in adult volunteers. Presented at the 34th Intersc. Conf. Antimicorb. Agents and Chemotherapy Abstract G91, p. 236.

Keyserling, H. et al. (1994) Immunogenicity of type 14 conjugate vaccine in infants. Presented at the annual meeting of the American Pediatric Society/Society for Pediatric Research Seattle, WA. Abstract 1087, p. 184A.

Kennedy, D. et al. (1994) Immunologic response to licensed pneumococcal polysaccharide vaccine (PS) in infants primed with heptavalent *Streptococcus pneumoniae* conjugated vaccine. Presented at the 34th Intersc. Conf. Antimicrob. Agents in Chemotherapy, Orlando Abstract G90, p. 236.

Kayhty, H. et al. (1995) Pneumococcal polysaccharide-menigococcal outer membrane protein complex conjugate vaccine is immunogneic in infants and children. J. Infect. Dis vol. 172, pp. 1273-1278.

Dagan, Ron et al. (1996) Reduction of Nasopharyngeal Carriage of Pneumococci during the Second Year of Life by a Heptavalent Conjugate Pneumococcal Vaccine. The Journal of Infectious Diseases vol. 174, pp. 1271-1278.

Sood, Ramesh K., et al., "Capsular Polysaccharide-Protein Conjugate Vaccines," Research Focus Reviews, DDT, Sep. 1996, pp. 381-387, vol. 1, No. 9, Elsevier Science Ltd.

Sarnaik, Sharada MD, et al., "Studies on *Pneumococcus* Vaccine Alone or Mixed With DTP and on *Pneumococcus* Type 6B and *Haemophilis influenzae* Type b Capsular Polysaccharide-Tetanus Toxoid Conjugates in Two Five-Year-Old Children With Sickle Cell Anemia," Pediatric Infect. Dis. J., vol. 9, pp. 181-6 (1990).

Andrew, P.W., et al., "Pneumococcal Vaccines," Freer et al. (Eds.), Bacterial Protein Toxins, Zbl. Bakt. Suppl. 24, 1994, pp. 453-466, Gustave Fischer, Stuttgart, Jena, New York.

Dagan, Ron, et al., "Reduction of Pneumococcal Nasopharyngeal Carriage in Early Infancy After Immunization with Tetravalent Pneumococcal Vaccines Conjugated to Either Tetanus Toxoid or Diphtheria Toxoid," Pediatr Infect. Dis. J., 1997, pp. 1060-1064, vol. 16, No. 11, Williams & Wilkins.

Lindberg, A. A., "Recent Trends in the Developments of Bacterial Vaccines," Brown F. (ed): New Approaches to Stabilisation of Vaccines Potency. Dev Biol. Stand. Basel, Karger, 1996, pp. 59-71, vol. 87.

Greenberg, David, P., et al., "Factors Influencing the Immunogenicity of a Pneumococcal Conjugate Vaccine in Infants +709," Pediatric Research: Apr. 1997—vol. 41—Issue 4, Part 2—p. 121; 1997 Abstracts The American Pediatric Society and The Society for Pediatric Research.

Ahman et al., Abstracts of the 35th ICAAC, 1995, G69, Immunogenicity of tetravalent pneumococcal (Pnc) conjugate vaccines (PndC, PncT) in Finnish infants.

Schutze et al, 1985, JI, vol. 135 (4), pp. 2319-2322.

De Velasco, Alonso, et al., Microbiological Reviews, 1995, pp. 591-603.

Insel, 1995, Annuals New York Academy of Science, pp. 35-47.

Galelli, et al., 1990, JI., pp. 2397-2405.

Barington, et al., 1993, Infection and Immunity, vol. 61 (2), pp. 432-438.

Di John, et al., 1989, The Lancet, Dec. 16, pp. 1415-1418.

Leclerc, et al., 1990, JI, vol. 145 (5), pp. 1343-1349.

Clemens, et al., 1995, Annuals New York Academy of Science, pp. 255-266.

Molrine, et al., 1995, Annals of Internal Medicine, vol. 123, pp. 828-834.

Anderson, et al., 2003, Vaccine, vol. 21, pp. 1554-1559.

Peeters, et al., 1996, Methods in Molecular Medicine, Vaccine Protocols, pp. 111-133.

Andre, 1999, Combination vaccines based on DTP, Novel enabling Technologies for Vaccine development, London, Jan. 26-27, 1999.

Anderson, et al., 1989, J. Immunol., vol. 142(7), pp. 2464-2468.

Butler, et al., 1994, J. Infect Dis., vol. 171(4), pp. 885-889.

Dagan, et al., 2004, Pediatr Infect Dis J, vol. 23, pp. 91-98.

Ellis and Granoff, 1994, Preface to developmnet and clincial uses of *Haemophilus* b conjugate vaccines, Marcel Dekker Inc.

Eskola et al., 1996, Lancet, vol. 348, pp. 1688-1692.

Todar, Kenneth, Department of Bacteriology, University of Wisconsin, Todar's online textbook of bacteriology, 2002, Immune defense against microbial pathogens.

Svenson and Lindberg, 1978, J. Immunol. Meth., vol. 25(4), pp. 323-335.

Svenson and Lindberg, 1981, Infect. Immun., vol. 32(2). pp. 490-496.

Wuorimaa, et al., 2001, J. Infect. Dis., vol. 184(9), pp. 1211-1215.

Wuorimaa, et al., 2005, Vaccine, vol. 23, pp. 5328-5332.

Schneerson, et al., 1984, Infect. Immun., vol. 45(3), pp. 582-591.

Cho, et al., 1995, 35th ICAAC San Francisco, p. 172, abstract.

Kuo, et al., Jul. 1995, Inl. Imm., vol. 63(7), pp. 2706-2713.

Eby, et al., 1994, Vaccine 94, Pneumococcal Conjugates Vaccine, Modern Approaches to New Vaccines Including Prevention of AIDS, Cold Spring Harbor Press, pp. 119-123.

Lindberg AA., 1991, "Polysaccharide vaccines: vaccines needed for the 1990s", In; R. Norrby (ed) Frontiers in Bacteriology, pp. 69-85.

* cited by examiner

MULTIVALENT VACCINE COMPOSITION WITH MIXED CARRIER

The subject of the present invention is a pharmaceutical composition intended for the treatment or prevention of a number of infections caused by pathogenic agents such as bacteria, which comprises, as immunogenic agent, polysaccharides derived from one or more pathogenic agent.

Bacteria as well as fungi such as yeasts incorporate polysaccharides into their surface structure. Thus, the great majority of bacteria are coated with an exudate of a polysaccharide nature which is attached to the bacterium more or less firmly but which is strictly speaking not an envelope. This exudate is called glycocalyx or capsule. Moreover, the outer membrane of Gram-negative bacteria, consists, inter alia, of lipopolysaccharide (LPS). Finally, polysaccharides are also found in the wall of fungi. These polysaccharides are in fact surface antigens which induce an immune response in an infected mammal.

Such polysaccharides are produced on the basis of units in which the constituents and the bonds are defined and which are characteristic of the bacterial or fungal species considered. These repeating units contain the epitopes, that is to say the structures which determine antigenicity.

The polysaccharides of pathogenic micro-organisms are reputed to be good vaccine agents. As they are, they are effective in adults and children over two years. On the other hand, in breast-feeding infants, some are only slightly or not immunogenic and do not induce any immune response. It is possible to overcome this problem by coupling, via covalent bonding, the polysaccharides to a so-called carrier protein such as diphtheria or tetanus toxoid so as to obtain a polysaccharide-carrier protein conjugate.

The same vaccine composition may contain several conjugates. Indeed, the trend is to combine several vaccinal agents intended to prevent or to treat infections induced by pathogenic agents from various species, this being, inter alia, in order to limit the number of administrations during the life of an individual. Furthermore, within the same species, there may be several serogroups/serotypes which are widely represented regionally or world-wide, It is this recalled that a serogroup/serotype is characterized, inter alia, by the nature of the capsule polysaccharide and that polysaccharides of various serogroups generally do not exhibit immunological cross-reactivity. In this case, it may therefore be necessary to combine the polysaccharides obtained from various serogroups in order to effectively combat an infection caused by one and the same species.

Thus, this is for example the case when it is sought to vaccinate against *Streptococcus pneumoniae* infections. Pneumococcal infections are a real public health problem especially since they are found in the severe forms of pneumonia, septicaemia and meningitis. In industrialized countries, they affect each year 30 to 100 per 100,000 children under three years. The mortality rate in cases of bacteraemia and meningitis is 15 to 30% whereas 5% of children die of pneumonia.

A study carried out in Finland from 1985 to 1989 shows that 90% of invasive infections are caused by 8 groups of serogroups/serotypes. Serogroups/serotypes 14, 6 and 19 are responsible for 54% of cases, serotype 14 being predominant in children under two years. Other pneumococci frequently isolated belong to serogroups 7, 18 and 23; yet others, more rare, belong to serogroups/serotypes 9 and 4. A similar distribution has been demonstrated in other industrialized countries, in particular in the United States.

Moreover, *Streptococcus pneumoniae* is responsible for a number of otitis infections which are more benign but very common. The number of children that have had an otitis infection before the age of six is evaluated at about 75% and the number of otitis infections caused by pneumococcus at 30 to 50%. In developed countries, otitis infections caused by pneumococcus are due to serogroup 19 in 25% of cases, followed by serogroups/serotypes 23 (13%), 6 and 14 (12%), 9 and 18 (4%) and 4 and 1 (2%).

A pneumococcal vaccine containing the polysaccharides of 23 serotypes is already commercially available. This vaccine makes it possible to effectively combat invasive infections in adults and has a transient action in children over seven months.

The capsular polysaccharides of pneumococci are T-independent antigens, i.e. they can induce antibodies, preferably of the IgM type, without the help of T cells and are not capable of promoting a booster response of the IgG type. When they are coupled to a carrier protein, these polysaccharides then prove capable of inducing a T-dependent response, most particularly in neonates and should provide long-term protection.

Clinical studies have been carried out in Finland and Israel with pneumococcal vaccines having four valencies containing conjugates 6B, 9V, 18C and 23F in which the polysaccharide was coupled either to Dt or to Tt. The doses were 1, 3 or 10 µg of polysaccharide per valency. Each of these formulations was administered simultaneously with an anti-*Haemophilus* vaccine (polyribitolphosphate coupled to Tt; Act-HIB marketed by Pasteur Merieux Connaught) and an anti-diphtheria, tetanus, whooping cough vaccine (for Finland, D. T. Coq marketed by KTL). Furthermore, these three administrations were carried out accompanied or not by simultaneous administration of an oral or injectable polio vaccine. They were repeated twice at a few weeks interval, and then once, one year after the first immunization.

The results of these studies as reported in the table below have made it possible to demonstrate an effect of negative interference of the diphtheria and tetanus toxoid load on the induction of anti-HiB antibodies, after the last immunization.

|  |  | Anti-HiB antibody in µg/ml |
|---|---|---|
| Finnish study |  |  |
| Placebo |  | 11.00 |
| Tetravalent pneumo |  |  |
| Tt: | 1 µg | 10.1 |
|  | 3 µg | 7.18 |
|  | 10 µg | 4.11 |
| Dt: | 1 µg | 11.5 |
|  | 3 µg | 12.5 |
|  | .10 µg | 7.18 |
| Israeli study |  |  |
| Placebo |  | 6.62 |
| Tetravalent pneumo |  |  |
| Tt: | 3 µg | 2.81 |
| Dt: | 3 µg | 4.62 |

A similar interference effect was observed during a clinical study in Iceland in which breast-feeding infants received Pro HIBit (PRP coupled to Dt; Connaught) in place of Act-HIB.

More generally, it is predicted that, regardless of the vaccine based on conjugated poly-saccharides, a maximum load of Dt and of Tt or of any other protein exists in the conjugated vaccine or in the association or combination of vaccine administered above which the immune response against polysaccharides conjugated with this protein may be reduced. In order to overcome the problem which the phenomenon of negative interference constitutes in multivalent vaccines composed of polysaccharide conjugates, the present application proposes to use not one but at least two carrier proteins so that the maximum load of each of the carrier proteins is not reached.

Accordingly, the subject of the invention is a composition comprising "n" conjugates C1 to Cn, each conjugate being composed (i) of a polysaccharide, in particular a polysaccharide derived from a *Streptococcus pneumoniae* serotype/serogroup S1 to Sn respectively, and (ii) of a carrier protein P1 to Pn respectively, "n" being a number equal to or greater than 2; in which composition the polysaccharides S1 to Sn are identical or different and in which the carrier proteins P1 to Pn are selected independently from a group consisting of "m" carrier proteins A1 to Am, "m" being a number equal to or greater than 2, provided that at least one of the carrier proteins P1 to Pn is different from the others.

According to another aspect, the subject of the invention is also a composition which comprises "n" conjugates C1 to Cn, each conjugate being composed (i) of a polysaccharide S1 to Sn respectively and (ii) a carrier protein P1 to Pn respectively, "n" being a number equal to or greater than 2; in which composition the polysaccharides S1 to Sn are identical or different and in which the carrier proteins P1 to Pn are selected independently from a group consisting of diphtheria (Dt) and tetanus (Tt) toxoids, provided that at least one of the carrier proteins P1 to Pn is different from the others; and which is characterized in that the quantity of Dt and Tt is respectively less than or equal to 200 and 50 µg/dose. In other words, a composition according to the invention comprises one or more polysaccharide conjugates in which the polysaccharide is coupled to the diphtheria toxoid (Dt) and one or more polysaccharide conjugates in which the polysaccharide is coupled to the tetanus toxoid (Tt) and is characterized in that the quantity of Dt and Tt is respectively less than or equal to 200 and 50 µg/dose.

By way of illustration, the following compositions are envisaged:

(i) A composition containing at least three conjugates C1, C2, C3, Cn, of formulas S1—P1, S2-P2, S3-P3, Sn-Pn, with: S1 to Sn identical to each other and P1 to Pn all different from each other;

(ii) A composition containing at least three conjugates C1, C2, C3, Cn, of formulas S1-P1, S2-P2, S3-P3, Sn-Pn, with: S1 to Sn all different from each other, P1 and P2 identical to each other, P3 to Pn identical to each other and P1 and P2 different from P3 to Pn, and (iii) A composition containing at least three conjugates C1, C2, C3, Cn, of formulas S1-P1, S2-P2, S3-P3, Sn-Pn, with: S1 and S2 identical to each other, S3 to Sn identical to each other, S1 and S2 different from S3 to Sn, P1 and P3 identical to each other, P2 to Pn, excluding P3, identical to each other and P1 and P3 different from P2 to Pn (—P3).

Thus, for the purposes of the present invention, the conjugates C1 to Cn, which are necessarily all different from each other, may be so in pairs either through their polysaccharide, or through their carrier protein or through their polysaccharide and their carrier protein. According to a specific embodiment, the polysaccharides used are all different from each other.

The number "n" of conjugates present in a composition according to the invention is equal to or greater than 2, and may in particular be equal to or greater than 3, 4, 6, 8, 10, 11, 12, 15 or 20. In general, this number "n" may be determined by persons skilled in the art as a function of a number of criteria in particular linked to the very nature of the composition, to the objectives which this composition should make it possible to achieve and to the population for whom this composition is intended. For example, in the case of a composition intended for treating or preventing pneumococcal infections in breast-feeding infants, it is considered that such a composition, in order to offer a good level of protection and world-wide protection, should contain at least 8, preferably at least 10, most preferably at least 11 valencies which may be represented by at least 11 conjugates or more.

"Polysaccharide" is understood to mean a polymer consisting of a plurality of saccharide repeating units, especially of more than four repeating units, regardless of the length of the saccharide chain and regardless of the average molecular weight of the polysaccharide. This term covers in particular that of oligosaccharide.

"Conjugate" is understood to mean a compound in which a polysaccharide is covalently linked to a carrier protein.

Thus, as previously stated, a composition according to the invention should use at least two carrier proteins. These carrier proteins may be chosen from all those commonly used in the field of vaccines. They may be in particular the diphtheria toxoid (Dt), the tetanus toxoid (Tt), the non-toxic mutant form CRM197 of the diphtheria toxin and the outer membrane protein type 1 (OMP1) of *Neisseria meningitidis* or any variant, analogue or fragment of the latter which has preserved the carrier capacity. The methods which make it possible to obtain these proteins in purified form are well known to persons skilled in the art. The terms "protein" as used in the present application applies to any amino acid chain, regardless of the length of the chain. In particular, this term covers the notion of peptide.

In general, the group of proteins A1 to Am from which the carrier proteins P1 to Pn are independently selected therefore represents all the proteins having a carrier effect. For their personal needs, persons skilled in the art may agree that their choice would be limited to a defined number of proteins and, consequently, they can define the group which they will use to make their selection on the basis of a number "m" of components equal to or greater than 2 and at most equal to "n", "n" being as defined above. In particular, persons skilled in the art can determine the minimum number of different carrier proteins which is necessary in order to avoid the phenomenon of interference. To do this, they will take into account the maximum load that should not be exceeded for each of the carrier proteins. "Maximum load" refers to the quantity of carrier protein above which a reduced immune response is observed against one or more polysaccharides compared with a corresponding monovalent composition (conjugate taken separately).

In particular, as regards the diphtheria toxoid and the tetanus toxoid, it is estimated that, advantageously, the quantity of these proteins present in a dose of a composition according to the invention should not exceed 200 and 50 µg respectively, such a dose being envisaged for administration in a mammal, preferably a human. Preferably, the Dt load is less than or equal to 150, 120 or 100 µg, most preferably 80 or 60 µg. Preferably, the Tt load is less than or equal to 35 or 25 µg, most preferably 20 or 10 µg.

Thus, it may be accepted that for a composition using only two different carrier proteins, the selection of these proteins will be made from a group consisting of proteins A1 and A2. Preferably, A1 and A2 may be diphtheria toxoid (Dt) and tetanus toxoid (Tt) respectively or vice versa.

According to a specific embodiment, a composition using only two different carrier proteins is characterized by a balanced distribution of the number of polysaccharides conjugated with the first carrier protein and of the number of polysaccharides conjugated with the second carrier protein. For example, when "n" is an even number, "n"/2 carrier proteins P1 to Pn are A1 and "n"/2 carrier proteins P1 to Pn are A2 or when "n" is an odd number, ("n"+1)/2 carrier proteins P1 to Pn are A1 and ("n"−1)/2 carrier proteins P1 to Pn are A2.

A polysaccharide useful for the purposes of the present invention may be in particular a polysaccharide of bacterial or fungal origin. It may be in particular a polysaccharide from *Streptococcus* e.g. *Streptococcus pneumoniae, Staphylococcus, Klebsiella, Salmonella* e.g. *Salmonella typhi, Escherichia, Shigella, Neisseria* e.g. *Neisseria meningitidis, Haemophilus* e.g. *Haemophilus influenzae, Moraxella, Vibrio cholerae* or *Mycobacterium tuberculosis.*

In a composition according to the invention, the polysaccharides may be derived from different species or alternatively may all be derived from the same species, e.g. from the same bacterial species, possibly of different serogroups/serotypes. In order to illustrate this last possibility, there may be mentioned a composition according to the invention intended to vaccinate against pneumococcal infections, which contains at least 8 valencies, preferably 10 or 11 valencies chosen from serotypes 1, 3, 4, 5, 6B, 7F, 9V, 14, 18C, 19F and 23F.

Thus, a composition constituting a pneumococcal vaccine advantageously comprises 10 or 11 valencies, e.g. represented by 10 or 11 conjugates in which the polysaccharides are all different from each other and are derived (have as origin) serotypes/serogroups chosen from serotypes 1, 3, 4, 5, 6B, 7F, 9V, 14, 18C, 19F and 23F of *S. pneumoniae.* It may be in particular a composition which comprises 10 or 11 conjugates selected from:

serotype 1 polysaccharide coupled to Tt or to Dt;
serotype 3 polysaccharide coupled to Dt;
serotype 4 polysaccharide coupled to Tt;
serotype 5 polysaccharide coupled to Tt or to Dt;
serotype 6B polysaccharide coupled to Dt;
serotype 7F polysaccharide coupled to Tt or to Dt;
serotype 9V polysaccharide coupled to Tt;
serotype 14 polysaccharide coupled to Dt;
serotype 18C polysaccharide coupled to Dt;
serotype 19F polysaccharide coupled to Tt; and
serotype 23F polysaccharide coupled to Dt.

Under another aspect, a composition constituting a pneumococcal vaccine may comprise 10 or 11 valencies represented by 12 to 22, especially 12 to 15 conjugates, in which the polysaccharides are derived from the serotypes chosen from serotypes 1, 3, 4, 5, 6B, 7F, 9V, 14, 18C, 19F and 23F, in which composition conjugates of the same valency differ from each other in the carrier protein. It may be in particular a composition which comprises:

serotype 1 polysaccharide coupled to Tt;
serotype 3 polysaccharide coupled to Dt;
serotype 4 polysaccharide coupled to Tt;
serotype 5 polysaccharide coupled to Tt;
serotype 6B polysaccharide coupled to Dt;
serotype 6B polysaccharide coupled to Tt;
serotype 7F polysaccharide coupled to Tt;
serotype 9V polysaccharide coupled to Tt;
serotype 9V polysaccharide coupled to Dt;
serotype 14 polysaccharide coupled to Dt;
serotype 18C polysaccharide coupled to Dt;
serotype 18C polysaccharide coupled to Tt;
serotype 19F polysaccharide coupled to Tt;
serotype 23F polysaccharide coupled to Tt; and
serotype 23F polysaccharide coupled to Dt.

Such a polysaccharide may be advantageously extracted from the microorganism according to conventional methods and purified likewise. This polysaccharide may be used in the crude form after extraction/purification. Alternatively, it may be fragmented in order to obtain a polysaccharide having an average molecular weight less than that of the polysaccharide originally extracted. A particularly advantageous fermentation method is described in WO 93/7178, now U.S. Pat. No. 6,007,818, which is incorporated by way of reference.

A conjugate in which a polysaccharide is coupled by covalent bonding to a carrier protein may be obtained according to conventional methods well known to persons skilled in the art. It may make use of a linker or a spacer to carry out the conjugation. Depending on the mode of conjugation used, the conjugate resulting therefrom may be a conjugate in which the polysaccharide is linked to the protein by a single chemical function (sun or neoglycoconjugate type), or by several functions (random coil type). It is within the capability of persons skilled in the art to determine the most appropriate mode of conjugation as a function of the nature of the polysaccharide and more particularly of the chemical groups carried by the polysaccharide which may be used during the conjugation reaction.

A composition according to the invention may be manufactured conventionally. In particular, it may be formulated with a pharmaceutically acceptable diluent or vehicle, e.g. water or a saline solution. In addition, the composition may contain customary ingredients such as a buffer, a preservative or stabilizer, an adjuvant such as an aluminum compound, e.g. an aluminium hydroxide, an aluminium phosphate or an aluminium hydroxyphosphate, and, where appropriate, a lyophilization excipient. In general, these products may be selected as a function of the mode and route of administration and based on standard pharmaceutical practices. Appropriate carriers or diluents as well as what is essential for the preparation of a pharmaceutical composition are described in *Remington's Pharmaceutical Sciences*, a standard reference book in this field.

A composition according to the invention may be administered by any conventional route which is used in the field of vaccines, in particular by the systemic, i.e. parenteral, route, e.g. by the subcutaneous, intramuscular, intradermal or intravenous route, or by the mucosal route, e.g. by the oral or nasal route.

The administration may take place in a single dose or in a dose repeated once or several times, e.g. once, twice or three times, after a certain interval of time. The appropriate dosage will vary as a function of various parameters, for example the number of valencies contained in the composition, the nature of the polysaccharide(s) used or the mode of administration. As a guide, it is indicated that good results may be obtained with per valency, a polysaccharide dose of 0.5 to 100 µg, preferably of 1 to 50 µg, most preferably of 1 to 10 µg. A dose of the composition according to the invention may be advantageously in a volume of 0.1 to 2 ml.

There are presented below, by way of example, various pneumococcal vaccines having multiple valencies, the valencies being chosen from serotypes 1, 3, 4, 5, 6B, 7F, 9V, 14, 18C, 19F and 23F. The polysaccharides derived from these serotypes were fragmented according to the method described in WO 93/7178. The polysaccharides coupled to Tt (except the type 1 polysaccharide) were coupled according to the conjugation method described in WO 93/7178. Briefly, a polysaccharide is subjected to reductive amination in the presence of sodium cyanoborohydride in order to link a molecule of diaminohexane to a terminal reducing group. The polysaccharide thus derived is then activated by a succinimide group using disuccinimidyl suberate (DSS). The polysaccharide thus activated is reacted directly with the carrier protein. The serotype 1 polysaccharide was coupled Dt to Tt [sic] according to the conjugation method described in U.S. Pat. No. 5,204,098 which is incorporated by way of reference. The other polysaccharides coupled to Dt were coupled as follows; hydrazide groups were incorporated onto the polysaccharide by reacting the polysaccharide with an excess of adipic acid dihydrazide (ADH) in the presence of ethyl dimethyl amino propyl carbodiimide (EDAC) and sodium cyanoborohydride (for all the types except 3) or simply in the presence of sodium cyanoborohydride (for type 3). The polysaccharide thus derived is reacted with the carrier protein in the presence of EDAC. The experimental conditions were controlled so as to obtain conjugates in which the quantity of protein is between one and four times, preferably twice, the value of the quantity of polysaccharide. Thus, for a dose, 3 µg of a particular polysaccharide are coupled to about 6 µg of Dt and 1 µg of a particular polysaccharide is coupled to about 2 µg of Tt.

The Dt and Tt used were prepared by detoxification with formaldehyde starting with toxins extracted respectively from *Corynebacterium diphtheriae* and *Clostridium tetani*.

The formulations contain a phosphate buffer (0.475 mg of $PO_4^{2-}$ ion per dose) and sodium chloride (4.5 mg per dose) and may be supplemented with aluminium hydroxide (alum) adjuvant (300 µg of $Al^{3+}$ ion per dose) and contain a preservative such as phenoxyethanol formalin. A dose is in the volume of 0.5 ml.

EXAMPLE 1

Octavalent Formulation

| Carrier protein | Polysaccharide Serotype | Quantity per single dose |
|---|---|---|
| Dt | 3 | 3 µg |
| Tt | 4 | 1 µg |
| Dt | 6B | 10 µg |
| Tt | 9V | 1 µg |
| Dt | 14 | 3 µg |
| Dt | 18C | 3 µg |
| Tt | 19F | 1 µg |
| Tt | 23F | 1 µg |

EXAMPLE 2

Formulations F3, F4 and F3bis Containing 11 Valencies

| Carrier Protein | Serogroup/ Serotype | Qty per single dose of formulation F3 (µg) | Qty per single dose of formulation F4 (µg) | Qty per single dose of formulation F3 bis (µg) |
|---|---|---|---|---|
| Tt | 1 | 1 | — | 1 |
| Dt | 1 | — | 3 | — |
| Dt | 3 | 3 | 3 | 3 |
| Tt | 4 | 1 | 1 | 1 |
| Tt | 5 | 1 | — | 1 |
| Dt | 5 | — | 3 | — |
| Dt | 6B | 10 | 10 | 3 |
| Tt | 6B | — | — | 1 |
| Tt | 7F | 1 | — | 1 |
| Dt | 7F | — | 3 | — |
| Tt | 9V | 1 | 1 | 1 |
| Dt | 9V | — | — | 3 |
| Dt | 14 | 3 | 3 | 3 |
| Dt | 18C | 3 | 3 | 3 |
| Tt | 18C | — | — | 1 |
| Tt | 19F | 1 | 1 | 1 |
| Tt | 23F | 1 | 1 | 1 |
| Dt | 23F | — | — | 3 |

The approximate protein load in each of the three formulations is as follows:

|  | F3 | F4 | F3 bis |
|---|---|---|---|
| Dt | about 40 µg | about 60 µg | about 40 µg |
| Tt | about 15 µg | about 8 µg | about 18 µg |

(which corresponds to a protein/polysaccharide weight ratio of about 2).

The invention claimed is:

1. A vaccine composition comprising a dose of "n" conjugates C1 to Cn, wherein
    (a) each conjugate comprises
        (i) a polysaccharide S1 to Sn from a *Streptococcus pneumoniae* serotype/serogroup, respectively, and
        (ii) a carrier protein P1 to Pn, respectively;
    (b) "n" is a number equal to or greater than 10;
    (c) the polysaccharides S1 to Sn are identical or there are from 2 to "n" different polysaccharides; and
    (d) the carrier proteins P1 to Pn are selected independently from a group consisting of "m" carrier proteins, wherein "m" is a number equal to or greater than 2;
    (e) at least one of P1 to Pn is Dt and at least one of P1 to Pn is Tt; and
    (f) the amount of conjugated Dt protein is less than or equal to 60 µg/dose and the amount of conjugated Tt protein in the composition is less than or equal to 25 µg/dose.

2. The composition according to claim 1, in which the conjugates C1 to Cn are all different from each other either by their polysaccharide, by their carrier protein, or by their polysaccharide and their carrier protein.

3. The composition according to claim 2, in which the polysaccharides S1 to Sn are all different from each other.

4. The composition according to claim 1 in which the carrier proteins P1 and Pn are independently selected from Dt and Tt.

5. The composition according to claim 4, in which when "n" is an even number, "n"12 carrier proteins P1 to Pn are a first protein and "n"/2 carrier proteins P1 to Pn are a second protein or when "n" is an odd number, ("n"+1)/2 carrier proteins P1 to Pn are a first protein and ("n"−1)/2 carrier proteins P1 to Pn are a second protein.

6. The composition according to claim 1, which comprises 10 or 11 conjugates in which the polysaccharides S1 to Sn are all different from each other and are chosen from serotypes 1, 3, 4, 5, 6B, 7F, 9V, 14, 18C, 19F and 23F of *S. pneumoniae*.

7. The composition according to claim 6, which comprises 10 or 11 conjugates selected from:
- serotype 1 polysaccharide coupled to Tt or to Dt;
- serotype 3 polysaccharide coupled to Dt;
- serotype 4 polysaccharide coupled to Tt;
- serotype 5 polysaccharide coupled to Tt or to Dt;
- serotype 6B polysaccharide coupled to Dt;
- serotype 7F polysaccharide coupled to Tt or to Dt;
- serotype 9V polysaccharide coupled to Tt;
- serotype 14 polysaccharide coupled to Dt;
- serotype 18C polysaccharide coupled to Dt;
- serotype 19F polysaccharide coupled to Tt; and
- serotype 23F polysaccharide coupled to Tt.

8. The composition according to claim 1 wherein n is 12 to 22 and the composition comprises 10 or 11 different polysaccharides S1 to Sn chosen from serotypes 1, 3, 4, 5, 6B, 7F, 9V, 14, 18C, 19F and 23F and in which conjugates having the same polysaccharide differ from each other in the carrier protein.

9. The composition according to claim 8, which comprises:
- serotype 1 polysaccharide coupled to Tt;
- serotype 3 polysaccharide coupled to Dt;
- serotype 4 polysaccharide coupled to Tt;
- serotype 5 polysaccharide coupled to Tt;
- serotype 6B polysaccharide coupled to Dt;
- serotype 6B polysaccharide coupled to Tt;
- serotype 7F polysaccharide coupled to Tt;
- serotype 9V polysaccharide coupled to Tt;
- serotype 9V polysaccharide coupled to Dt;
- serotype 14 polysaccharide coupled to Dt;
- serotype 18C polysaccharide coupled to Dt;
- serotype 18C polysaccharide coupled to Tt;
- serotype 19F polysaccharide coupled to Tt;
- serotype 23F polysaccharide coupled to Tt; and
- serotype 23F polysaccharide coupled to Dt.

\* \* \* \* \*